United States Patent [19]

Talmore

[11] Patent Number: 5,344,434

[45] Date of Patent: Sep. 6, 1994

[54] APPARATUS FOR THE PHOTODYNAMIC THERAPY TREATMENT

[75] Inventor: Eli T. Talmore, Ramat-Alon, Israel

[73] Assignee: Technion Research & Development Foundation, Ltd., Israel

[21] Appl. No.: 994,619

[22] Filed: Dec. 21, 1992

[30] Foreign Application Priority Data

Dec. 29, 1991 [IL] Israel ............................. 100,545

[51] Int. Cl.$^5$ ............................................. A61N 5/00
[52] U.S. Cl. ..................................... 607/88; 607/89; 606/3; 606/13
[58] Field of Search .................. 607/88–94; 606/3, 2, 9–13, 16–18

[56] References Cited

U.S. PATENT DOCUMENTS

| | | | |
|---|---|---|---|
| 3,693,623 | 9/1972 | Harte et al. | 606/9 |
| 4,630,273 | 12/1986 | Inoue et al. | 607/89 X |
| 4,926,861 | 5/1990 | Fenyo et al. | 607/88 |
| 4,930,504 | 6/1990 | Diamantopoulos et al. | 606/3 X |
| 5,010,452 | 4/1991 | Krebser et al. | |
| 5,217,455 | 6/1993 | Tan | 606/9 |

FOREIGN PATENT DOCUMENTS 8900796  7/1989  PCT Int'l Appl. .

*Primary Examiner*—Angela D. Sykes
*Attorney, Agent, or Firm*—Morgan & Finnegan

[57] ABSTRACT

The invention relates to an apparatus for an efficient photodynamic therapy treatment. The apparatus comprises the following parts: (a) a lamp possessing a narrow beam light with half angle divergence up to 10°, possessing an intensity of at least 2 mW/nm with a spectral region in the range of 610 to 750 nm; (b) a glass lens to focus the beams of the light; (c) a red filter possessing a transmittance of 0.95 which provides a spectral region of above 610 nm, and (c) a light guide in the range of 3 to 12 mm diameter, which provides a minimum irradiance of 50 mW/cm$^2$. According to a preferred embodiment the lamp is provided with a fixed internal reflector. In order to transmit the useful radiation and to remove the heat produced by the infra-red radiation, a 45° dicroic mirror is attached to the apparatus.

11 Claims, 2 Drawing Sheets

APPARATUS FOR THE PHOTODYNAMIC THERAPY TREATMENT

The present invention relates to photodynamic therapy treatment. More particularly, the invention relates to an efficient apparatus for the photodynamic therapy treatment of a wide range of solid tumors.

BACKGROUND OF THE INVENTION

Photodynamic therapy (hereinafter referred to as PDT), is a relatively novel type treatment developed in the last ten years for certain types of cancer, including skin cancer and breast cancer. The PDT treatment is based on the systemic or topical administration of a tumor-localizing photosensitizer reagent, such as porphyrins, which after illumination and excitation with visible light in the presence of oxygen, give rise to highly reactive and cytotoxic molecular species. These cytotoxic molecular species damage sensitive targets within the tumor, producing cell death and subsequent tumor necrosis.

The early clinical work used a wide range of filtered and unfiltered light, sources, but it was concluded that a laser light was necessary in order to produce monochromatic light of the appropriate wavelength at high power levels which could be transmitted via a flexible fiber. The delivery dose will obviously depend on the area of tumor to be treated and the power of the laser. Generally a minimal delivery dose of 12 mW/cm$^2$ is mentioned to be necessary, although there are cases where satisfactory clinical results have been obtained using also a lower dose. The total energy dose is quite empirical, but it is suggested that for superficial skin lesions, a total dose in the range of 25 to 50 J/cm$^2$ may be appropriate, whereas for exophytic ulcerated lesions, a total dose of 100–200 J/cm$^2$ is thought to be necessary.

To-day it is considered that PDT has to be introduced as the first arm of treatment of tumors on the human body.

A very recent publication WO 90/00420, describes an apparatus for a light delivery system, applicable to medical treatment techniques which rely on the illumination of body tissue in order to achieve photodynamic therapy and biostimulation. The apparatus comprises a source for illuminating the surface and means for scattering light reflected from the surface so that it can be directed back onto the surface. Preferably, the source for illuminating is a laser and the reflecting surface has a concave shape. Most preferably, the light source is the tip of an optical fiber which is arranged in a manner which could illuminate the diffusely reflective surface so that the light resulted from the laser is reflected towards the area to be treated. However, laser systems suffer from some important drawbacks being quite expensive, especially for an ambulatory apparatus, and the illumination obtained is characterized by its non-homogeneity. Moreover, there is no evidence whatsoever that for PDT treatment, there are required the specific qualities possessed by laser, as opposed to non-coherent conventional lamps, such as monochromacity or temporal coherence.

The use of laser diodes is claimed in the U.S. Pat. No. 4,930,504 for biostimulation of tissue. The apparatus used comprises an array of monochromatic radiation sources which provide a first wavelength of less than 830 nm, a second wavelength greater than 830 nm and a third wavelength greater than 900 nm.

Another recent U.S. Pat. No. 5,010,452 describes a therapeutic lamp for biostimulation with polarized light. The light source is mentioned that has to possess a power in the range of between 30 W and 300 W. The apparatus described seems to be quite complicated to be useful as an ambulatory device for the PDT treatment.

The above brief review of some references from the prior art, clearly indicates the long felt need for a simple apparatus useful for the PDT treatment.

It is an object of the present invention to provide a simple apparatus useful for the treatment of PDT. It is another object of the present invention to provide a simple apparatus which is capable to supply a broad band radiation, useful for an efficient treatment of PDT. It is yet another object of the present invention to provide a simple apparatus useful for the treatment of PDT, which does not require any skilled technician for its smooth operation.

BRIEF DESCRIPTION OF THE INVENTION

The invention relates to an apparatus for an efficient photodynamic therapy treatment, which comprises:
- a lamp possessing a narrow beam light with half angle divergence of up to 10°, possessing an intensity of at least 2 mW/nm with a spectral region in the range of 610–750 nm;
- a glass lens to focus the beam of the light;
- a red filter to provide a spectral region of above 610 nm, and
- a light guide in the range of 3 to 12 mm diameter, which provides a minimum irradiance of 50 mW/cm$^2$.

It was found that this apparatus is very useful for PDT treatment with many photosensitizers, such as chlorins and phtalocynins, and not only with polyfirins as mentioned in the prior art. The resulting irradiance from the apparatus is much higher than that of the commonly used laser sources and as a consequence, the number of the PDT treatments applied is significantly reduced. Due to the wide divergence of the lamp radiation, the applied radiation is evenly distributed over the illuminated area thus resulting in a uniform exit beam. The apparatus is very safe and no risk of accidental injury to the operator or patient, which might occur with a laser system, would be involved.

DESCRIPTION OF THE DRAWINGS

The invention will be further described by way of non-limitative example with reference to the accompanying drawings wherein.

DESCRIPTION OF A PREFERRED EMBODIMENT

Figure 1:
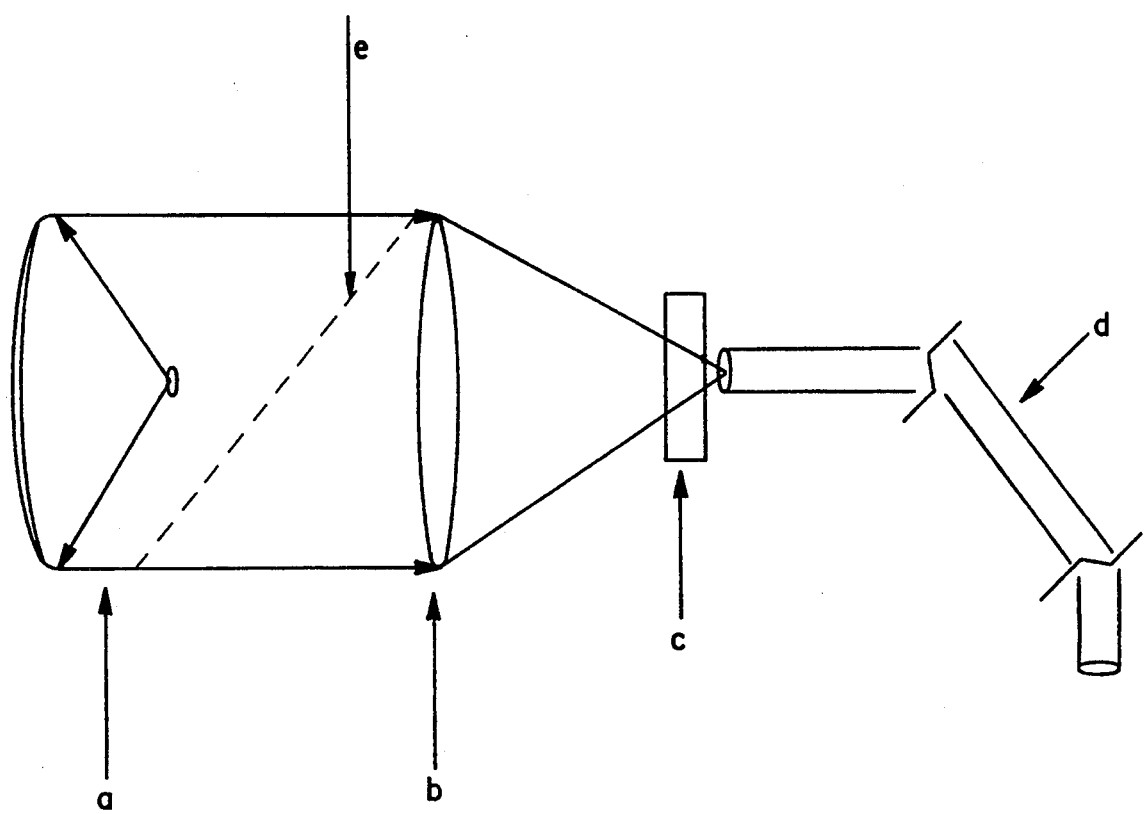
FIG. 1, is a schematic illustration of the apparatus according to a preferred embodiment of the present invention.

A detailed description of a preferred embodiment will be hereinafter presented in conjunction with the above FIG. 1.

The apparatus comprises the following four components:
Item (a) is lamp possessing a narrow beam light with half angle divergence up to 10° and having an intensity of at least 2 mW/nm. Optionally, a fixed internal reflector is provided in order to impart a further increase to the light intensity. A typical lamp which would provide a useful narrow beam light is a rugged Xenon short arc lamp of 150 W with an output of 2.8 W in the range of 610–750 nm. The lamp spectral irradiance in the visible portion of the spectrum is slowly varying with wavelength.

Item (b) is a glass lens, which has the role to focus the beam of the light. Generally, it possesses a transmittance of about 0.95.

Item (c) is a red filter—known as high-pass filter— which provides a spectral region of above 610 nm and does eliminate from the beam of the light all the radiation below 610 nm wavelength. This filtration is absolutely required in order to reduce the undesired radiation on the patients skin and will transmit only the red radiation. As known, the red radiation penetrates more efficiently through the skin layer. Most preferably, the transmittance of the red filter is about 0.95.

Item (d) is a light guide made from a flexible tube, filled with an anaerobic fluid, having a diameter in the range of 3 to 12 mm, and preferably above 5 mm, when it absorbs the radiation above 750 nm.

According to another embodiment, the red filter (item c) provides a spectral region in the range of 610–750 nm. In this case, the light guide (item d), having the same diameter, is made from a flexible tube filled with glass or fused silica.

According to a most preferred embodiment, a 45° dicroic mirror (UV-Vis transmitting and IR reflecting) is also provided in order to transmit the useful radiation and to remove the heat-producing infra-red radiation.

Figure 2:
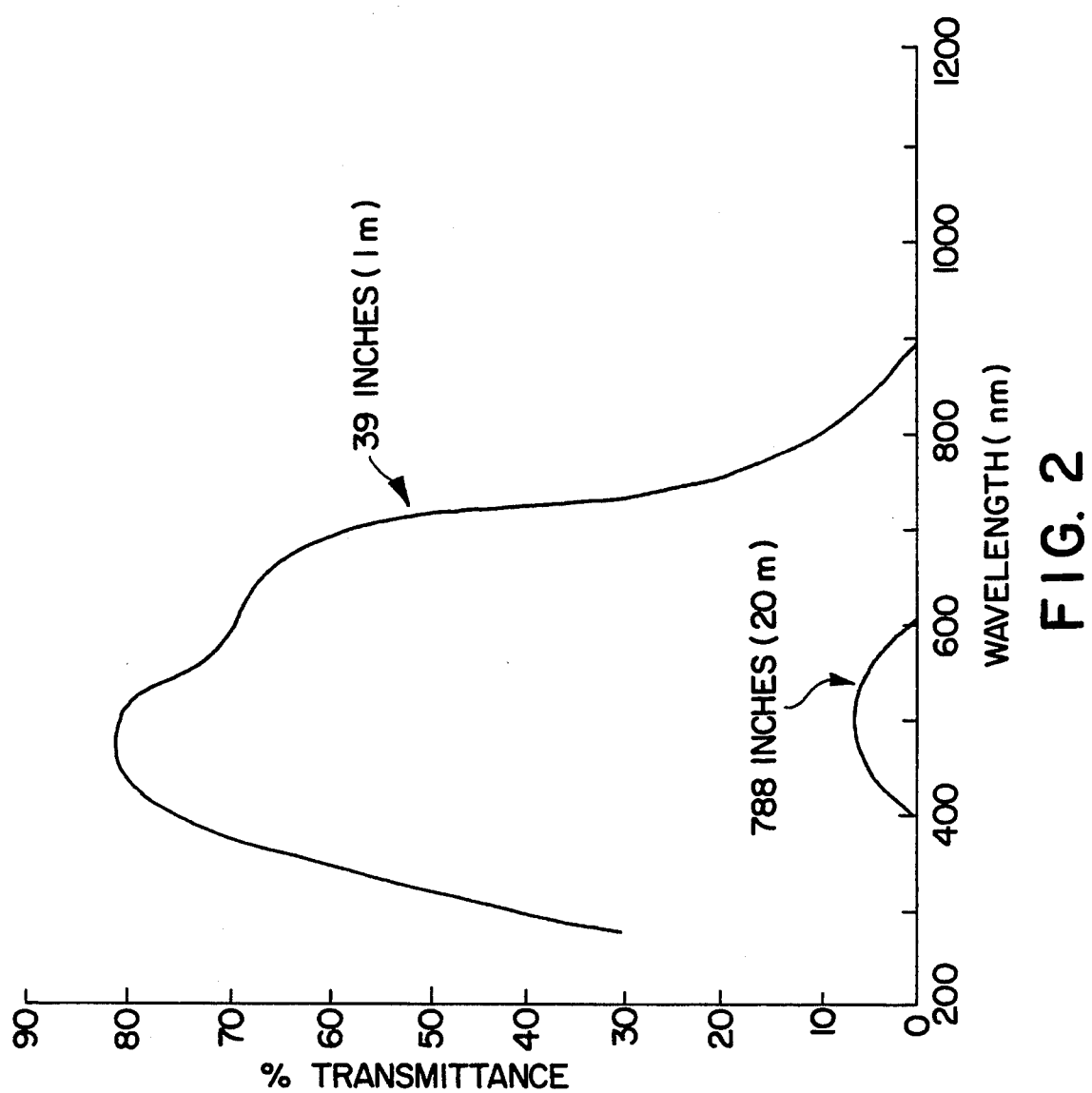
FIG. 2, correlates the percentage of transmittance as a function of wavelength for a liquid light guide.

FIG. 2, is a typical transmittance of the liquid light guide, which filtrates out the transmittance of the wavelength above 750 nm. Although the light guide absorbance removes the infra red radiation, its internal heating decreases the useful life-time of the device. In order to prevent the heating of the light guide, a 45° dicroic mirror is used. This component has a typical transmittance of 0.85. If the light beam is focussed on the entrance edge of the light guide, then the output will have a very narrow angular divergence, similar to the laser beam. In some applications, a broad uniform beam illuminating larger areas is required. In this case, the entrance of the light guide is moved towards the lens. This defocussing will result in a loss being about 45%. The output beam is uniformly divergent, a typical one being a full angle of 50°.

The overall efficiency of PDT treatment according to the present invention, is much higher than that obtained by the use of a monochromatic laser treatment, being of a factor of 7.7. This value appears from the following compared data:

Using phtalocynine as a photosensitizer, wherein the relative efficiency at 630 nm is 0.1, with a laser irradiance of 50 mW/cm$^2$, the useful treatment irradiance, so called overall efficiency, will be 5 mW/cm$^2$. The relative efficiency of PDT is defined as the product of the photosensitizer absorption efficiency and skin transmittance of 2 mm thickness.

When using the lamp according to the present invention, which possesses a spectral irradiance of 0.9 mW/cm$^2$/nm, an absorption efficiency of 43 nm (in the wavelength range of 610–750 nm) will exist. Therefore, the overall efficiency will be:

$$0.9 \times 43 = 38.7 \text{ mW/cm}^2$$

The consequence of this high efficiency will be a considerable decrease in the time required for the PDT treatment.

An important advantage of the apparatus according to the present invention, is the fact that the irradiation is applied selectively onto the skin area which has to be treated, generally in the range of 5 to 10 cm$^2$, while healthy areas are protected from potentially harmful radiation.

Although the apparatus has been described particularly for the treatment of solid tumors wounds of a cancerous type, one may conceive to use the apparatus also for biostimulation treatment. It will impart a beneficial effect in speed-up healing of wounds, ulcers and physiotherapy. Of course, in case of biostimulation which requires a irradiance of 15 to 20 mW/cm$^2$, the intensity of the lamp (item a) should be lower.

In some applications, especially where the tumor is not visible directly, its detection is required before the PDT treatment is applied. It is well known that the fluorescence-based tumor diagnostics is a beneficial technique, where a 340–410 nm light source is employed. By incorporating a special filter for the above region, the apparatus for the photodynamic treatment will include the diagnostics means. Since both violet rays (390–410 nm) as well as red rays (610–750 nm) channels are emitted through the same light guide, a most convenient operation would be achieved.

Another envisaged use is for blood sterilization, whereby a photo phyrin binding to a virus will occur followed by a subsequent irradiation by red light, thus resulting a virus destruction.

An additional advantage of the apparatus, is the fact that it can be considered ambulatory, due to its small dimensions and accordingly can be used on patients at home without requiring skilled personnel.

The apparatus may also be further improved by connecting it to a microprocessor, as a control unit, which enables a smooth and automatic operation. The microprocessor also controls the time exposure and program treatment as well as the number of treatments scheduled for a complete curing. In this manner, it will be possible by monitoring the time of the treatment, to deliver the correct dose of light, irrespective of the beam dimensions and independently of the loss of radiant output of the lamp with time. The initiation of the lamp is given by a pressure sensitive sensor, which starts the operation only when the skin is touched, thus avoiding the application of light to undesired location.

Although the invention has been described in respect with some specific embodiments, it should be understood that a person skilled in the art may introduce some changes without being outside the scope of the invention, as covered by the appended claims.

I claim:

1. An apparatus for an efficient photodynamic therapy treatment which comprises:

a lamp emitting a narrow beam light with half angle divergence up to 10°, said beam possessing an intensity of a least 2 mW/nm with a spectral region in the range of 610–750 nm;

a glass lens to focus the beam of the light;

a red filter interposed between said lamp and a light guide, said red filter providing a spectral region of above 610 nm from said beam of the light, and said light guide having a diameter in the range of 3 to 12 mm, which provides a minimum irradiance of 50 mW/cm$^2$.

2. The apparatus according to claim 1, wherein said lamp is provided with a fixed internal reflector.

3. The apparatus according to claim 1, wherein said glass lens possesses a transmittance of 0.95.

4. The apparatus according to claim 1, wherein the transmittance of the red filter is about 0.95.

5. The apparatus according to claim 4, wherein the red filter provides a spectral region in the range of between 610–750 nm, the light guide being made from a flexible tube filled with a material selected from the group consisting of glass and fused silica.

6. The apparatus according to claim 1, wherein the light guide is made from a flexible tube filled with an anaerobic fluid.

7. The apparatus according to claim 1, wherein said lamp is a Xenon lamp.

8. The apparatus according to claim 1 used in combination with a photosensitizer that is topically applied on skin which will receive the photodynamic therapy treatment, said photosensitizer selected from the group consisting of chlorins, phtalocynins and polyfirins.

9. The apparatus according to claim 1, wherein a 45° dichroic mirror is present in order to transmit the useful radiation and to remove heat produced.

10. The apparatus according to claim 1, further comprising a microprocessor controller which controls the apparatus for an automatic photodynamic therapy treatment.

11. The apparatus according to claim 10, wherein said microprocessor monitors the time of treatment to ensure that the correct dose of light is delivered.

* * * * *